(12) United States Patent
Heffelfinger et al.

(10) Patent No.: US 7,016,087 B2
(45) Date of Patent: Mar. 21, 2006

(54) PHOTON EFFICIENT SCANNER (75) Inventors: David M. Heffelfinger, Oakland, CA (US); Aram P. Schiffman, San Ramon, CA (US); Bala S. Manian, Los Altos Hills, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 951 days.

(21) Appl. No.: 09/925,124

(22) Filed: Aug. 8, 2001

(65) Prior Publication Data

US 2003/0030850 A1   Feb. 13, 2003

(51) Int. Cl.
*H04N 1/04*   (2006.01)

(52) U.S. Cl. .................. 358/474; 358/484; 250/458.1; 250/459.1; 250/461.1

(58) Field of Classification Search ................ 358/474, 358/484, 513; 250/458.1, 459.1, 461.1, 461.2; 359/208, 196
See application file for complete search history.

(56) References Cited

U.S. PATENT DOCUMENTS

| | | | |
|---|---|---|---|
| 4,281,924 A | | 8/1981 | Auer et al. ..................... 356/73 |
| 4,959,824 A | * | 9/1990 | Ueda et al. ................ 369/44.14 |
| 4,979,824 A | * | 12/1990 | Mathies et al. ............. 356/318 |
| 5,371,020 A | | 12/1994 | Frischauf .................... 436/165 |
| 5,547,849 A | * | 8/1996 | Baer et al. .................. 435/7.24 |
| 5,556,764 A | | 9/1996 | Sizto et al. ................. 435/7.24 |
| 6,078,420 A | * | 6/2000 | Macken ....................... 359/208 |
| 6,750,457 B1 | * | 6/2004 | Heffelfinger et al. .... 250/458.1 |

* cited by examiner

*Primary Examiner*—Kimberly Williams
*Assistant Examiner*—Negussie Worku
(74) *Attorney, Agent, or Firm*—Schneck & Schneck; Thomas Schneck; David M. Schneck (57) ABSTRACT

A system for optical interrogation of a sample adaptable for multiple wavelength illumination and multiple wavelength fluorescent or luminescent light collection, wherein the illumination wavelength profile and the light collection profile may overlap. In the system, coherent light from one or more lasers is focused onto a target layer on a sample to excite fluorescent or luminescent light from the target layer. Emitted light is collected from a selected depth by a reflective light collector that transmits the collected light to detection optics. The reflective light collector directs collected light at an angle to the optical axis of the illumination light, thereby separating collected emitted light from illumination light. The light collector may collect light from a focus, whereby the focused illumination light combined with the focused light collection aid in limitation of the depth of field to a selected depth. Additionally, a spatial filter positioned between the light collector and the detection optics may be used to confine the depth of field to a selected depth. This device may be incorporated into an optical scanner by scanning of illumination light in a first direction and translation of the sample in a tangent direction. Alternatively, the illumination and detection optics may remain stationary and the detectable targets moved past a scanning location (e.g. as in electrophoretic analysis).

27 Claims, 4 Drawing Sheets

PHOTON EFFICIENT SCANNER

TECHNICAL FIELD

The present invention relates to optical scanning systems and specifically to optical scanning in a limited depth of field.

BACKGROUND OF THE INVENTION

Optical scanning has provided a rapid, sensitive method for the analysis of a variety of targets. Optical analysis has a variety of features advantageous to current analytical requirements. These include:

1. Rapid scanning capability. An illumination beam may be optically moved in a line scan across a sample. As the beam moves across a layer on the analyzed substrate, the excited fluorescence from the sample is measured. This allows optical scanning systems to image discrete illumination areas in a rapid scan.

2. High sensitivity. The use of fluorescent detection provides a sensitive means of detecting a variety of targets. A fluorescent or other optically detectable dye may be conjugated to a variety of binding or labeling agents. The use of labels with specific optical signals provides for discrimination of the target both in vitro and in vivo. Conjugation of the optical label to a binding agent allows for optical detection with the selected specificity of the binding agent.

3. Imaging versatility. The use of optically detectable labels may be adapted to a number of different imaging formats. Optical detection may be employed in bioarrays, where binding to a spot on a surface is indicated by an optical signal. Alternatively, a binding agent may be used in a solution for binding to a solid substrate or cell.

4. Processing throughput. Optical scanning interrogates a discrete area of a substrate in a rapid scan. Such scanning is adaptable to multiplexing, with use of different dyes, arrays of reaction containers (e.g. wells on a multi-well plate), and pooling of samples to be analyzed all available as means to increase sample processing throughput. Automation of placement of analytical substrate on a stage for optical interrogation allows further increase in the sample processing, enabling automated high throughput assays.

One system for optical sample scanning is described in U.S. Pat. Nos. 5,547,849 and 5,556,764. In this system, a laser illumination beam is reflected by a beam splitter, and focused by an objective lens onto a sample container or substrate. Excited fluorescent light is gathered by the objective lens (which also acts as a light collector) and transmitted as a retrobeam to the beam splitter. The beam splitter is designed to reflect the excitation beam while transmitting the collected emission light. The beam passes through the beam splitter and is directed through a focal lens, which focuses the light through an aperture of a spatial filter and onto detection optics. The spatial filter acts to block emission light that originates from outside an interrogated depth of field from reaching the detection optics. The objective, spatial filter and illumination focus optics act in conjunction to limit the depth of field to a narrow plane.

The focal optics focus the illumination into a beam spot that concentrates the illumination energy into a selected depth. The objective will collect and collimate light originating from this depth. Out of focus emission light will not be focused through the aperture of the spatial filter and onto the detectors. In contrast to confocal imaging that images a depth of field of under 1 um, the depth of field of the described system is between 25–250 um. This provides a "virtual capillary" from which fluorescence may be detected.

This system provides a number of advantages for imaging. First, the limitation of detection to a thin detection depth allows for homogenous assay (i.e. no separation step). A sample mixture may contain a fluorescent binding agent that is present in an assay mixture both bound to a discrete target (e.g. a cell or solid substrate) and is also present free in solution. Because detection is limited to a narrow depth of field, the unbound optically detectable binding agent is detected only as a background signal. The greater concentrations of binding agent present at target binding sites produce a sufficient optical signal to allow detection over a background signal. The ability to perform a homogenous assay increases sample processing throughput by avoiding time consuming washing steps. In addition, possible error or cross contamination from washing steps is eliminated. Also contact with sample is minimized. This reduces risks from infectious or toxic samples.

A second advantage is versatility of the system. Although the system in the patents is described as scanning a capillary of limited depth, the described system may be adapted for optical analysis in a limited depth of a variety of sample containers or substrates.

A third advantage of the system is simplified alignment. When the illumination beam is in focus on its target, the resulting fluorescence, which originates from the same focal spot, is automatically in focus. The objective that focuses the illumination beam also acts as the light collector. Illumination and light collection optical alignment are never a problem because a single element serves a dual function of both illumination focus and emission light collection. This design also minimizes the space required for the optics and reduces the required number of optical elements, reducing system costs and assembly difficulty.

Despite these advantages, the described optical configuration presents certain limitations. In the present configuration a number of optical elements are common to both the illumination beam path and the detection (retrobeam) path. Thus eventually the illumination light must be optically separated from the fluorescent emission to allow detection. This may be achieved using a beam splitter, such as a coated dichroic mirror that reflects the excitation beam to the objective and transmits the excitation retrobeam to the detection optics. This requires design of this element to be compatible with only specific illumination sources and excitation wavelengths.

In certain applications it may be necessary to use different combinations of excitation wavelengths and different combination of dyes producing different emission wavelengths. However the beam splitter must be selected for a specific excitation and emission combination. To use different filters would require a very precise filter wheel. Because the alignment of this element is critical for proper targeting of the illumination beam, movable filters are technically impractical.

Alternatively, a dot mirror having a reflective dot surrounded by a transmissive element could be used. The illumination laser beam is much smaller than the diameter of the emitted fluorescence retrobeam. The illumination beam would thus be reflected while the outer annulus of the retrobeam is transmitted through the transmissive elements to the detection agents. In this design, multiple illumination and emission wavelengths are accommodated in a design that is intrinsically compatible with a broad wavelength range for both illumination and light collection. A broad spectrum of illumination wavelengths would be reflected by the central reflective element and a broad spectrum of emission wavelengths transmitted through the transparent annular disc.

However certain drawbacks to this system design are also expected. First, part of the retrobeam is blocked by the reflective center reflective mirror, resulting in a loss of signal. Because the energy of the signal is concentrated at the center, this loss would be significant. In addition, the objective must be broadly achromatic to allow for it to both focus the illumination beam and collect and collumnate the retrobeam. This creates design difficulties to produce an objective lens which is both efficient in light collection while also being broadly achromatic to allow both focus of the illumination light and collection of the emission light.

It is the object of the present invention to provide a photon efficient optical scanner which illuminates a sample and collects light from a large numerical aperture. It is a further object to provide a scanner that may be used with a variety of different illumination and emission wavelengths without changing optical elements. It is a further object of the invention to provide a scanner which could be adapted to scan a variety of sample media, including solid substrate surfaces, wells of a multiwell plate, capillaries, or other sample containers. It is a further object of the invention to describe a scanner that scans in a limited depth of field (allowing for homogenous assay of discrete targets). This scanner should be compact, versatile, allow for high speed scanning, and be adaptable to automation.

SUMMARY OF THE INVENTION

The above objects are achieved with a scanner that employs achromatic elements for light collection, and directs the collected light to a pathway divergent from the illumination light. By separation of the illumination light from the collected light, the system eliminates the design problems inherent in having optical elements that must be suitable for illumination transmission or focusing and light collection.

In one embodiment of this design one or more lasers are used to produce illumination light. If multiple lasers are used, the beams are optically combined. In one embodiment, separate shutters may be used to allow single laser illumination. A line filter may be placed in the path of each beam to ensure fidelity of the illumination wavelengths.

A portion of the laser beam is directed to a power monitor, which monitors laser power output and allows normalization of collection data for laser power fluctuation. If multiple lasers are used, the power of each laser may be separately monitored (for example by splitting the laser beam, using laser shutters to monitor each laser separately, or by separately directing each laser to the power monitor).

The portion of the illumination beam that is not diverted to the power monitor is directed through the illumination beam shaping optics. The beam shaping optics focus the illumination light into a beam spot that is focused onto the sample of interest. In one embodiment, the beam spot shaping optics is a zoom expander/contractor lens that may produce a variety of different beam spot sizes. The focused illumination light is then directed onto a beam scanning optic. This scanning optic moves the focused illumination beam in a line scan. The beam is then directed through an objective lens and onto the sample of interest. The illumination beam excites fluorescent light from the sample of interest. The focus optics concentrates the illumination energy into a limited depth of field onto the sample of interest.

The excited fluorescent light is collected by a reflective element. The reflective element collimates the collected light and directs the light to detection optics. The reflective light collector preferably is a curved surface that will collect and collimate light only within a specific focal depth. This depth is matched with an aperture acting as a spatial filter to block out of focus light (e.g. light originating outside of the depth of field) from reaching the detectors.

The reflector is broadly reflective across a wide range of wavelengths. This facilitates collection of a broad spectrum of wavelengths, from the infrared through the visible spectrum. It is preferred that the light collector have a pass through hole to allow the illumination beam to pass through the collector such that the illumination beam is not transmitted to the detector elements. In one embodiment the light collector is an off-axis paraboloid mirror placed such that the illumination focal spot and the mirror focus are the same depth. This can provide a highly efficient collector that acts in conjunction with the focused illumination light to confine the scan depth to a limited depth of field. This light collector allows photon efficient light collection.

The combination of three optical elements act to limit the depth of field. First, the illumination beam is focused by a lens and the illumination beam waist is targeted onto the depth of interest. This concentrates illumination energy within a limited depth. Second, the light collector is designed to collimate and reflect to detection optics fluorescent emission from substantially the same depth. Finally, the collumnated collected emission light is focused through the aperture of a spatial filter. Out of focus light originating outside of the selected depth will be blocked by the spatial filter. The three elements act in combination to limit detection to a selected depth of field.

Emission light within the light collector's depth of focus is collimated by the light collector and directed through a detection lens. The lens focuses the collected emission light through an aperture of a spatial filter. The spatial filter acts to block out of focus light from reaching the detector. The detector measures the intensity of the emission light. In one embodiment, the emission light is divided into component wavelengths above and below a threshold wavelength. The intensity of each component is separately detected and the ratio of the intensity is used to characterize the emission.

DETAILED DESCRIPTION OF THE INVENTION

In the present invention, an optical scanner has been developed which is capable of scanning in a limited depth of field, allowing analysis of cells, spots on an array (e.g. nucleic acid arrays) or other discrete particles. The depth of field is limited by three optical elements that act in combination. First, the illumination is provided by laser light that is focused to concentrate the illumination energy to a limited depth. Second, the light collector is selected to collect and transmit emitted light only from a limited depth. Third, the emission light is focused through an aperture. The aperture width is matched to the illumination and light collection optical elements to confine the depth of detection to a selected depth. The sample is scanned within a depth that may be selected to be from 25 to 250 um deep. This allows the rapid analysis of a volume for discrete optically detectable targets.

Figure 1:
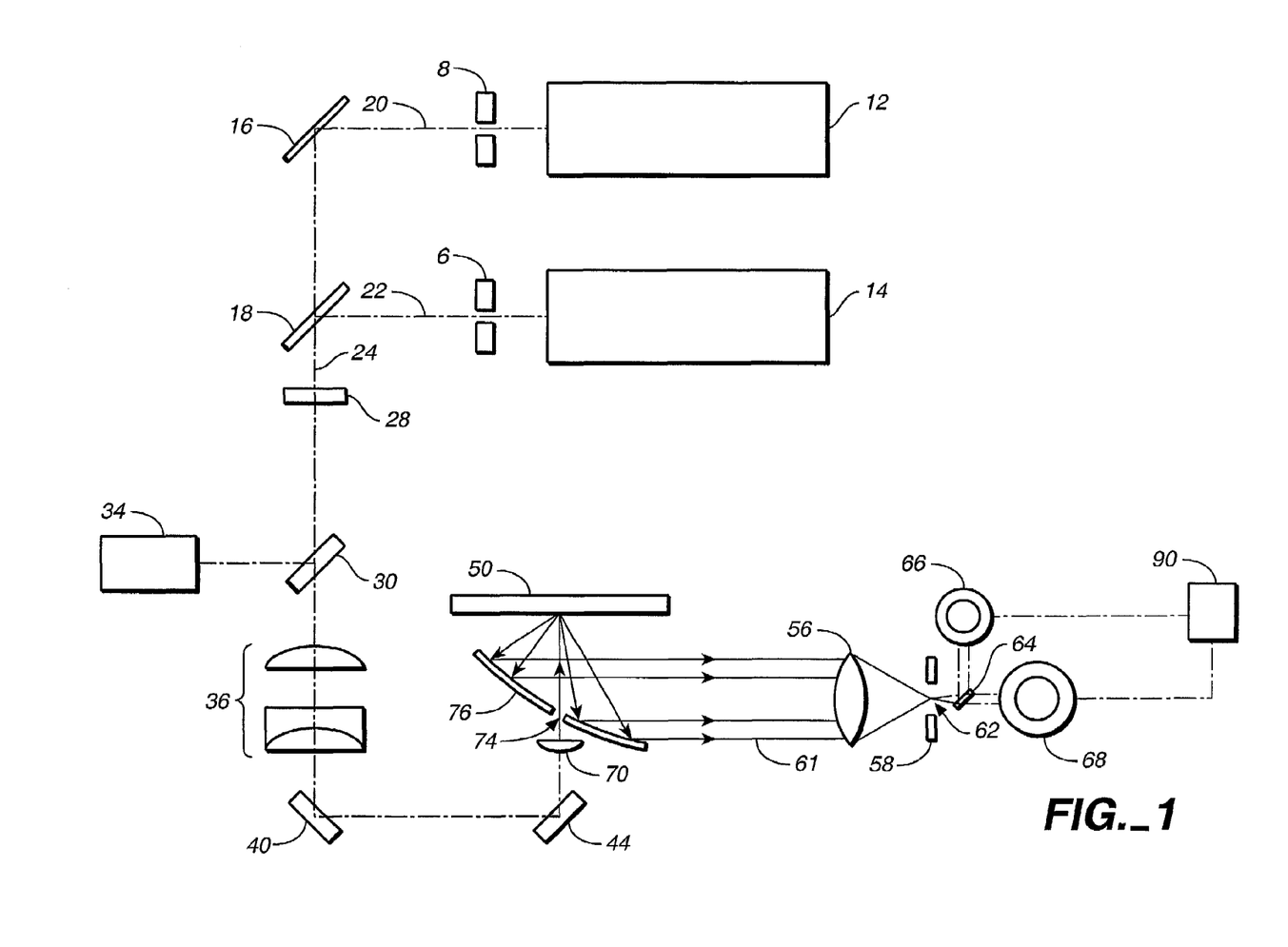
FIG. 1 is a schematic of one embodiment of the optical scanning system.

An example of the system utilizing these features is illustrated in FIG. 1. A first laser 12 produces a first laser beam 20. Beam 20 is directed by steering mirror 16 to dichroic mirror 18. A second laser 14 produces a second laser beam 22 that is directed to dichroic mirror 18. Dichroic mirror is selected to reflect laser light 22 and transmit laser light 20, thereby combining the beams into illumination beam 24. Shutters 8 and 6 may be used to block transmission of beams 20 and 22 respectively. This would allow illumination with only one of the lasers.

Figure 2:
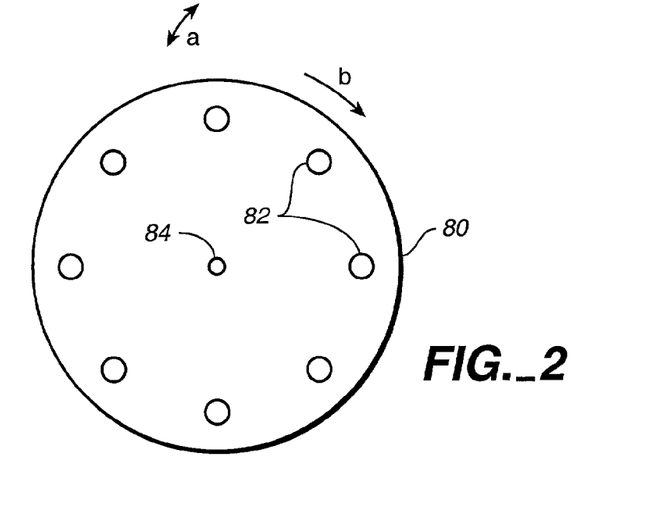
FIG. 2 illustrates a filter wheel.

The illumination beam 24 is directed through laser line filter 28. Laser line filter 28 ensures laser beam 24 wavelength fidelity. Alternatively, separate laser line filters could be used for each laser. Such filters would be placed in the laser beam path between the laser and the beam combining optics. FIG. 2 represents another alternative for selection of laser filters. In this embodiment, a number of different filters 82 are disposed on a filter wheel 80 that rotates on a hub 84. Different optical filters may be rotated into the pathway of the laser as indicated by arrow b. In addition, the wheel may be angled, as indicated by arrows a, in the pathway of the laser. This alters the effective thickness of filter and may be used to "tune" the filter to optimal properties.

Returning to FIG. 1, the illumination beam is directed through beam splitter 30 that directs a portion of the beam to power monitor 34. Power monitor 34 monitors the intensity of the illumination beam output. Data gathered from the power monitor could be used to subsequently normalize the emission light intensity to correct for fluctuations in illumination intensity. The shutters may be used to block one laser beam while measuring the output of the other laser. In this way, the output of each laser may be separately monitored. If the filter wheel of FIG. 2 is used, power monitor may continuously monitor the illumination beam power as the filter is changed or moved, to determine the effect of the filter on the illumination beam intensity.

The portion of the illumination beam that is not diverted to power monitor 34 by beam splitter 30 passes through zoom expander/contractor optic 36. These elements are configured to shape the beam spot. The beam spot may be tailored to the size of the target to be investigated. A central processor may automatically control the zoom expander/contractor optic 36.

The beam is focused by the expander/contractor optic 36 and passes onto mirror 40. Mirror 40 directs the beam onto steering mirror 44 that directs the illumination beam through achromatic doublet lens 70 and onto the sample containing substrate 50. The achromatic doublet lens 70 is selected such that the index of refraction for the illumination wavelengths would not affect the targeting of the illumination light. Because the illumination beam is focused with a low numerical aperture (less than 0.05) an inexpensive commercial achromatic doublet lens can be used to provide broadband, achromatic focusing of the illumination beam. Typically less than 1% variation in focal length is found in achromatic doublets from 400–1000 nm. Zoom expander/contractor optic 36 and achromatic doublet 70 focus the coherent illumination light into a beam spot. Focused beam 24 concentrates the illumination energy in the region of the beam waist. Outside of this region, the illumination energy concentration rapidly declines.

The focused light beam passes through a hole 74 in light collector 76 and is focused onto a target surface 50. As seen in FIG. 1, the achromatic focus lens 70 is located behind the off axis paraboloid. This location avoids blocking emission light collection, which would occur if the lens were positioned in front of reflecting surface. The target surface may be part of a sample holding container (e.g. a well bottom in a multi-well plate or a targeted surface in a rectangular capillary or a cuvette), a substrate (e.g. a biochip or glass slide array) or an analytical device storing radiant images (e.g. a storage phosphor screen).

In one embodiment the focused beam waist is moved relative to the sample such that the beam is scanned over a two dimensional surface. Because the system images a specific depth, the scanning of a two-dimensional surface allows the optical interrogation of a volume in a container. This two dimensional scan may be effected in several ways. For example, the sample may be moved in two dimensions (e.g. along a width and length dimensions of a flat substrate). As the sample is moved relative to the fixed beam waist, different areas of the sample are illuminated. Various stages that would allow such movement of the sample are known.

Figure 5:
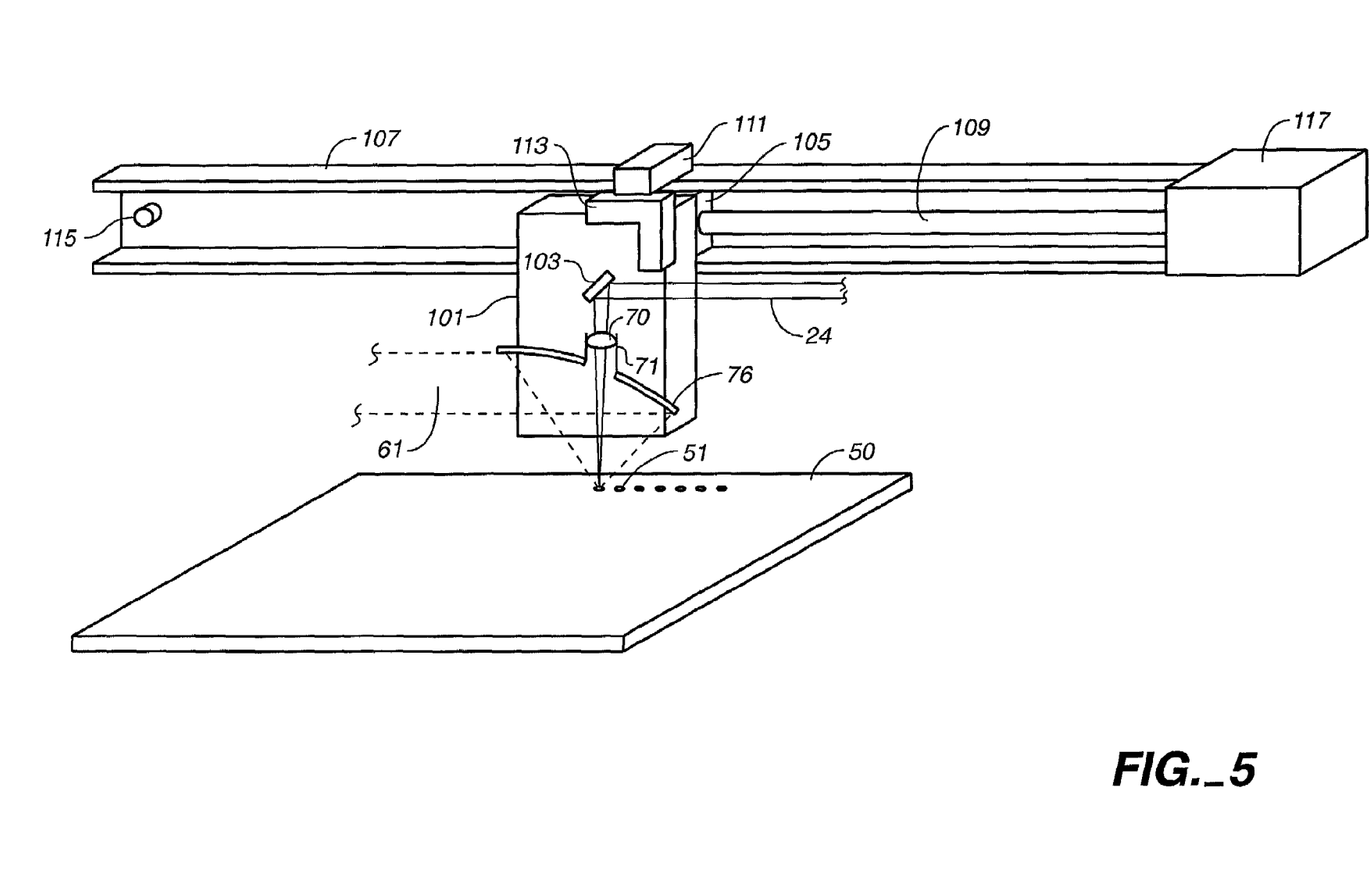
FIG. 5 illustrates a scanning device for the present invention.

A second method of moving the sample in relation to the beam waist is shown in FIG. 5. In this embodiment a light collection optic is mounted on a moving platform. The platform is mounted on a track. This configuration allows a line scan of the beam. By moving the sample in a tangent direction the beam waist may be scanned over a two dimensional surface.

In FIG. 5, mounted on a light weight platform is a steering mirror 103 and the curved reflective light collector 76 with an associated mount 71 holding achromatic doublet 70. Steering mirror 103 and light collector 76 are in a fixed position on platform 101. Platform 101 is mounted on a bearing 105 that slides on track 107. Track 107 is shown as a channel. Actuator 117 is attached at one end of track 107 and is mechanically attached to platform 101 by bar 109 that is joined to bearing 105. Actuator 117 is directed by a central electronic control (not shown) to move the platform in a back and forth motion on track 107. Pin 115 is positioned at the end of track 107 distal from actuator 117. Pin 115 is a physical barrier preventing bearing 105 from leaving track 107. Track 117 and the associated elements are mounted within is system such that platform 101 such that the optic elements attached to platform 101 may direct the illumination light onto the sample and collect emission light from the sample. Collimated illumination light 24 is directed by the illumination optics (as shown in FIG. 1) to steering mirror 103, which directs the illumination beam through achromatic doublet 70 through the hole in collection mirror 76 and onto sample substrate 50. The illumination beam excites fluorescent dyes from array spots 51 on sample 50. Reflective light collector 76 collects the emitted fluorescent light and transmits the collected illumination light as a collimated emission beam 61 to detection optics.

The movement of platform 101 along track 107 provides a scan of the illumination beam in a first direction. A sample holding stage (not shown) may incrementally translate sample substrate 50 in a tangent direction. This allows movement of the beam in a two-dimensional scan over the surface of the sample. The stage movement may be effected by a lead screw connected to a motor or other similar device. The optical path of the illumination light and collected emission light is continually lengthened and shortened as platform 101 moves along track 107. The lightweight platform 101 may be rapidly moved along a single axis. Available actuators for movement along one axis allow movement of 100 inches per second. This could produce a operational range of 5–25 Hz. Such actuators would include lead screws attached a reciprocating motor, as well as cams, belts, cranks or other mechanical actuators.

The scanning method illustrated in FIG. 5 allows the illumination and collection of light at a fixed angle to the sample. This provides some advantages over alternate scanning mechanisms. For example, if a galvanometer mirror or other optical scanning (reciprocal movement of the scanning beam are used), the light moves through a given angular arc. To ensure that the light remains targeted on the sample, the optical configuration must relay the reciprocating beam. This may be affected by sets of telescoping lenses that act to ensure the beam is targeted on the sample. By scanning the focus lens and light collector, these elements are eliminated.

Returning to FIG. 1, in the exemplary system the focused light beam concentrates illumination energy within a limited depth. The width of the beam spot is the width of the waist of the focused beam. The illumination light will excite fluorescence from the illuminated area (i.e. depth and width illuminated by the focused beam spot). Light collector 76 will collect some of the emitted fluorescence. Preferably light collector 76 is an off-axis paraboloid mirror. The mirror is broadly reflective (achromatic), allowing reflection of a broad spectrum of emitted light to the detection elements. The paraboloid has a focus from which the reflector will collect and collimate light. The light collector focus is matched to the focal depth of the illumination optics such that both illumination energy concentration and light collection occurs in the same depth of field. In the illustrated embodiment, a hole through the light collector allows the beam to pass through the light collector. This hole is relatively small (a few mm) and causes minimal loss in the collected light efficiency. Fluorescence entering the hole is lost (i.e. will not reach the detection elements), but the surface area of the hole is small compared to the remaining surface area of the off-axis paraboloid. In an alternative design, the focus illumination and the light collection optics could be placed on opposite sides of the substrate being analyzed. Again a hole in the reflective light collector would allow the illumination light to pass through and not be reflected onto the detector.

The collected light is collimated by the light collector 76 and transmitted as a collimated beam to detection focus lens 56. This lens focuses the light through aperture 62 in spatial filter 58. This spatial filter may act to block out of focus light from reaching the detectors. The aperture in spatial filter is a selected size and position to allow light collection only from a specific depth. The spatial filter, light collector and illumination focus optics act in conjunction to limit the depth of detection to a limited depth of field. The emission light that is focused through the aperture passes onto a beam splitter 64. Beam splitter 64 separates the emission light into components above and below a cutoff wavelength. Thus for example, emission light above a threshold wavelength could be detected by detector 66 and emission light below a threshold wavelength could be detected by detector 68. Each of the detectors could be a photo multiplier tube, a photo diode, or other light detection element.

The detectors are attached to a central memory that converts the analog detection signals to digital data and stores the intensity measurement information. The recorded intensity measurement may be stored as a ratio of the intensity measured by each detector. The ratio would be characteristic of the dye or combination of dyes measured by each detector. U.S. Pat. No. 5,556,764; hereby expressly incorporated by reference herein; details a method of characterizing an optical signal using a linear regression analysis of the ratio of two spectral components of collected emitted light.

Alternatively, the detection optics could use segmented detectors, CCD devices or other light intensity measuring optics to measure the light intensity. U.S. patent application Ser. No. 09/318,494; hereby expressly incorporated by reference for all purposes herein; describes a number of different optical elements for measuring light intensity. For example a prism may be used to separate emission light into spectral components. The intensity of a number of different spectral components is detected by a segmented detector. The profile of these intensity measurements may be used to characterize the emission signal. In a related embodiment, a direct vision prism is used with a segmented detector to allow detection of the intensity of a central, undedicated wavelength spectrum as well as refracted light. Again, the intensity profile of the various spectra detected allows characterization of the emission light as characteristic of a specific dye.

In FIG. 1, a spatial filter having an aperture is used to block out of focus light from reaching the light detector. In an alternative embodiment, an optical fiber may be used to limit the depth of field. Like a spatial filter, an optical fiber has an optical aperture (i.e. rays of light will pass through the optic from a defined cone of meridional rays). Light near the focus of the paraboloid will be reflected as a collimated beam and then focused into the optical fiber. Emission light originating outside of the focus of the paraboloid will either physically miss the tip of the fiber or will impinge on the fiber at an angle at which the light does not propagate. Since the numerical aperture of the fiber may be selected, the sensitivity of the detection system in accepting emission light may be similarly tailored.

Figure 4:
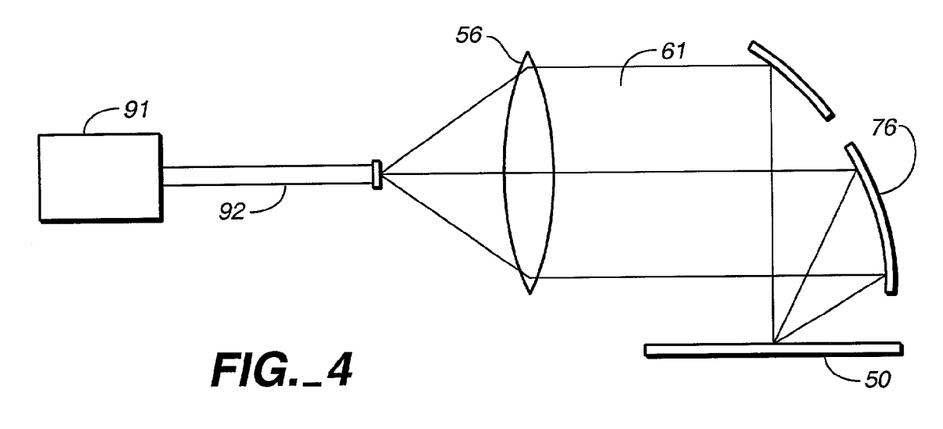
FIG. 4 illustrates an optical fiber used in light collection.

With reference to FIG. 4, the light emission from substrate 50 is collected and collimated by parabolic mirror 76. Emission light that originates from the focal depth of the mirror is collimated and directed onto focus lens 56. Lens 56 will focus the collimated emission light into the tip of optical fiber 92. Rays impinging on optical fiber 92 at an angle which allows propagation will be transmitted to detector 94. Detector 94 measures the intensity of the impinging light.

In one embodiment the sample holding substrate is translated in a first direction and the optical scan of the beam scans in a tangent direction, producing a line scan of the analyzed depth. This scan illuminates and excites emission light from the selected depth. The data recorder measures the light intensity at regular intervals, allowing assay of the entire depth. It is preferred that the data recorder measure light intensity at intervals which are sufficiently frequent to allow for each measurement to include a partial overlap with the previous measurement. In this manner the light emission intensity from overlapping spots is detected. U.S. Pat. No. 5,547,849; hereby expressly incorporated by reference herein, describes one method in which a sample is analyzed and data is recorded from a sample.

In FIG. 1, a bottom scanning system is shown. It would also be possible to rotate the position of steering mirror 44 and the light collection and detector optics by 180 degrees, allowing top down scanning. In addition, a 90 degree rotation would allow sideways scanning of a vertical sample. In the illustrated system, the illumination beam passes through the back of the reflective light collector and is transmitted through the sample. It is also possible to configure the described scanner such that the illumination and scan optics are on one side of sample and the collection and detection optics are on the other side of the sample. The illumination light would again pass through the sample and pass through a beam dump (e.g. beam pass through hole in the reflective light collector).

The present system presents several advantages over previous optical detection systems. The system may be used with a broad range of illumination and emission wavelengths. The system allows optical interrogation in a limited depth of field. As a result, the background fluorescence from unbound reagents may be distinguished from target events. This feature allows for homogenous assays, greatly increasing system throughput. A final key feature of the system is a high numerical aperture light collector that allows for sensitive detection across a broad range of wavelengths.

The reflective light collector allows for a efficient light collection. In prior systems in which the excitation beam and collected light share a pathway, the objective acts to both focus the illumination light and to collect the emitted fluorescence. The objective lens size and position determine the numerical aperture from which light is collected. The chromatic properties of the lens limit the illumination and emission wavelengths that may be efficiently collected. The reflective light collector, in contrast, is inherently achromatic and will collect all wavelengths equally. In addition, the reflective light collector could be larger and positioned closer to the sample than would be practical for an objective lens. This gives the reflective light collection a wide angle and large surface for light collection providing efficient light collection by the reflective light collector. These combined features allow the reflective light collector to have a high numerical aperture of light collection.

As noted, a key advantage of the system is detection in a limited depth of field. The present system may detect targets from a depth ranging from 1 to 500 um. This allows detection of a wide range of cells, beads, assay spots or other discrete targets.

Figure 3:
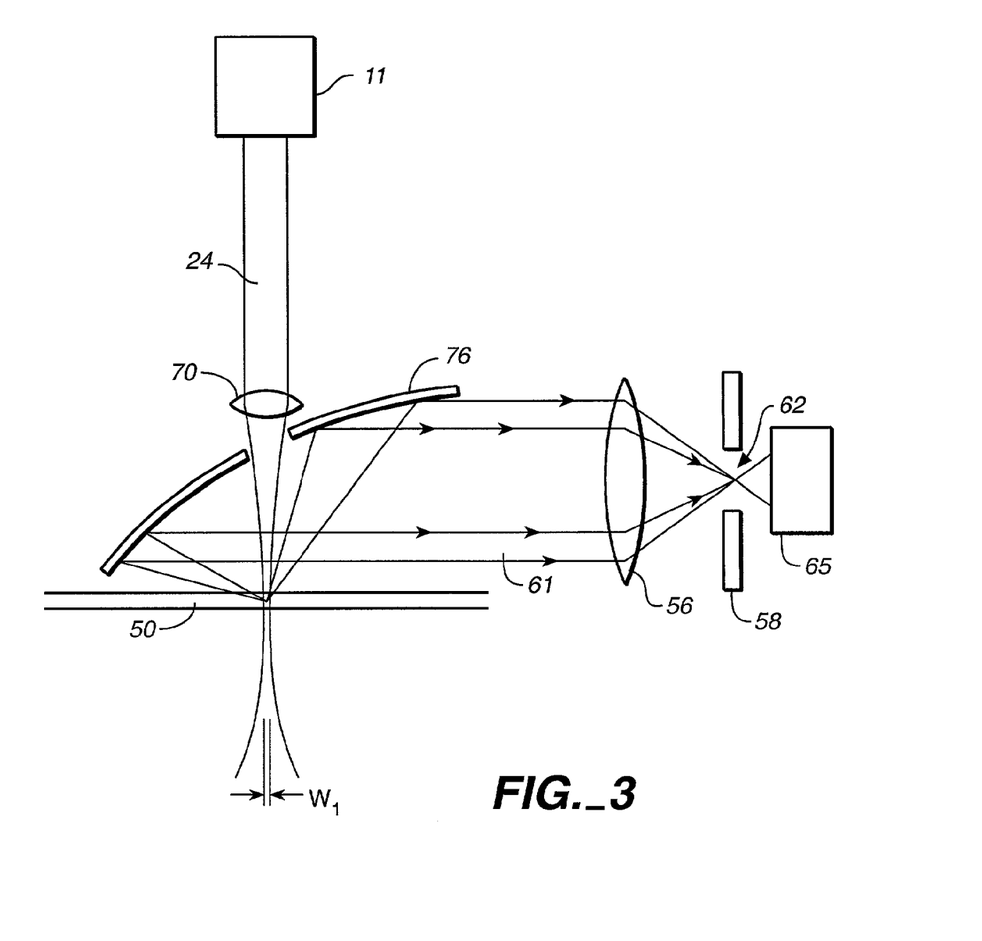
FIG. 3 shows a detail of the schematic illustrating illumination and light collection within a limited depth of field.

FIG. 3 illustrates the combined optical elements that allow for both efficient light collection with a high numerical aperture light collector and limitation of the analyzed depth of field. The illumination laser 11 produces an illumination beam 24, which is directed through doublet lens 70. This lens is selected to be broadly achromatic, allowing for focusing of a broad band of illumination wavelengths. The illumination light is focused into a Gaussian waist. The illumination energy is most concentrated at the narrowest part of the waist. Outside of this area, the illumination energy rapidly falls off. The waist of the focused illumination light is targeted onto a surface of substrate 50. As previously noted, substrate 50 could be the bottom of a microplate well (e.g. nucleic acid arrays associated with a microplate well bottom), the bottom of a cuvette, a capillary surface, the surface of an array slide, a biochip, or the analytical substrate. If a capillary or bioanalytical chip is used, the present examples have illustrated movement of the optics in a first direction and the substrate in a second direction to allow for a two dimensional scan. It is also possible to move a fluorescent sample (e.g. by electrophoresis, flow cytometry, etc.) by the scanning optics. Migrating samples would be detected as the samples move past a scanning beam. The illumination light 24 excites fluorescence from discrete targets associated with the surface. Such targets could be fluorescently labeled cells, fluorescent beads, or labeled spots on an array, or other optically detectable targets.

The emitted light is collected by light collector 76. As shown, the reflective light collector may be designed both to collect a wide range of emission ray angles and to be positioned proximate to the target substrate. A reflector is inherently broadly achromatic and a broad band of wavelengths will be collected and transmitted by light collector 76. The parabolic light collector has a focus. Light emanating from the focus is collected and reflected as a collimated beam to the detection elements. Locating the light collection focal point within the illumination focal depth limits detection to a selected depth of field.

In the assay container, an assay mixture may contain both fluorescent label bound to a target and unbound fluorescent reagent in solution. Within the depth of detection, a target may be distinguished by the relatively high concentration of the fluorescent label at a binding target compared to the lower levels of the fluorescent label in the surrounding assay mixture. In some containers, the depth of the container results in a column of assay mixture that is many times the depth of the target layer. If fluorescence was detected from this column of liquid, the background of unbound fluorescence could be sufficient to mask possible target event signals. By limiting the detection to a limited field of view, the targets may be detected in homogenous assays (i.e. assays which do not require a washing step to remove unbound fluorescent reagents).

The light collector 76 collimates the collected light and directs the collimated beam 61 to a detection lens 56, which focuses the collected light through an aperture 62 in a spatial filter 58. Light rays that are out of the focal depth will be blocked by the spatial filter and will not pass through to the light detector. Collected light that is in focus will pass onto light detector 65 and the intensity of the light will be measured.

Three elements in combination act to limit detection to a limited depth of field. First, the illumination light is concentrated into a beam waist that is targeted onto the layer to be optically interrogated. Second, the light collector is shaped to also have a focus, which is matched to the focal depth of the illumination light. Finally, the collection optics use an optical aperture to block out of focus light from reaching the detectors.

Given the limited depth of field of the present system, the ability to focus on a targeted surface is needed to allow for sample analysis. The ability to autofocus would allow the targeted surface or layer of interest to be positioned within the system focal depth. On method to focus onto the target layer is disclosed in U.S. patent application Ser. No. 09/430, 418, hereby expressly incorporated by reference herein. This patent application details the use of surface specular reflection to determine focus on a surface of interest. As the target surface is moved perpendicular to the illumination beam focal spot, specular reflection from the surface is detected by the beam power monitors. The specular reflection maximum intensity will be measured when the waist of the illumination beam is targeted on the surface of interest. The surface may then be positioned for optimal illumination and scanning as required for the specific assay.

We claim:

1. An optical scanner for scanning a fluorescent sample associated with a sample container, said scanner comprising:
   at least one laser producing an illumination beam;
   an illumination focus lens, focusing said illumination into a beam spot said beam spot targeted on the fluorescent sample;
   a reflective light collector positioned proximate to said sample container and in a path of said illumination beam that collects light from a collector focus and reflects collected light as a collimated emission beam, wherein said light is reflected at an angle in relation to an optical axis of said illumination beam, said light collector having a hole that allows said illumination beam to pass through said reflective light collector; and light detection optics, said light detection optics detecting the intensity of said emission beam.

2. The optical scanner of claim 1, further comprising:
a beam scanner that moves the beam spot in a scan through a layer in said container;
a spatial filter placed in the emission beam said spatial filter transmitting a portion of said focused emission light;
a detection lens positioned in the path of the collimated emission beam between said light collector and said spatial filter, wherein the detection lens focuses collimated light through the spatial filter.

3. The optical scanner of claim 2, wherein said beam scanner includes a scan head comprised of platform onto which said reflective light collector is mounted, a track supporting said platform and an actuator that drives the platform on the track.

4. The scanner of claim 3, further comprising a stage for holding the sample container, said stage translating the container in a direction tangent to a beam scan direction.

5. The optical scanner of claim 2, wherein said beam scanner includes a stage that translates the sample container in two dimensions.

6. The optical scanner of claim 2, wherein said spatial filter is provided by an optical fiber end.

7. The optical scanner of claim 2, wherein said spatial filter includes an aperture.

8. The optical scanner of claim 1, wherein said illumination focus lens is an expander/contractor lens allowing shaping of the illumination beam spot size.

9. The optical scanner of claim 1, wherein said illumination focus lens is achromatic.

10. The optical scanner of claim 1, wherein said reflective light collector is paraboloid mirror.

11. The optical scanner of claim 10, wherein said paraboloid mirror has a hole through which the illumination beam may pass.

12. The optical scanner of claim 1, further comprising an electronic memory for storing detection intensity measurements.

13. The optical scanner of claim 1, wherein said light detection optics includes a beam splitter and at least two light detectors, wherein the beam splitter directs the emission wavelengths above a threshold wavelength to a first light intensity detector and wavelengths below a threshold wavelength to a second light intensity detector.

14. The optical scanner of claim 13, wherein said light intensity detector is a photomultiplier tube.

15. The optical scanner of claim 1, wherein the depth of detection is limited to a depth of field between 1 and 500 nm.

16. The optical scanner of claim 15, wherein the reflective light collector has a focus point within said beam spot.

17. The optical scanner of claim 1, further comprising a beam splitter placed in the path of the illumination beam and diverting a portion of the illumination beam and a power monitor positioned in the path of the diverted illumination beam.

18. The optical scanner of claim 1, wherein at least one laser comprises a first and a second laser and a reflective beam combining optic, said beam combining optic merging laser beams from said first and second laser into a single illumination beam.

19. The optical scanner of claim 18, further comprising a first and a second shutter placed in front of each laser beam from said first and second laser.

20. A method to optically interrogate a sample having discrete, optically detectable targets the method comprising:
directing a focused laser light beam onto said sample;
moving said focused laser light in relation to said sample such that a waist of said focused laser light moves through an area of said sample;
collecting fluorescent emission with a reflective light collector, said light collector having a focal depth, said light collector collimating said collected light into a collimated emission beam; which is directed to an angle relative to an illumination light beam to detection optics; and
measuring an intensity of the collected emission light.

21. The method of claim 20, further including focusing said collimated emission beam through a spatial filter having an aperture through which a percentage of impinging light may pass, said spatial filter limiting the depth of field to a selected depth.

22. The method of claim 21, wherein focusing said collected light through an optical device having an aperture includes focusing said collected light into an optical fiber.

23. The method of claim 21, wherein focusing said collected light through an optical device having an aperture includes focusing said collected light through a pinhole aperture in a spatial filter.

24. The method of claim 20, wherein collecting light with a reflective light collector includes collecting light with a parabolic mirror.

25. The method of claim 20, further comprising analyzing the intensity of collected emission light to identify discrete optically detectable targets.

26. The method of claim 20, wherein said sample is a homogenous assay mixture.

27. The method of claim 20, further comprising prior to moving said focused laser light, focusing a beam waist of said focused laser light onto a defined layer in said sample.

* * * * *